United States Patent [19]

Goff et al.

[11] Patent Number: 4,562,386
[45] Date of Patent: Dec. 31, 1985

[54] CURRENT SENSE DEMODULATOR

[75] Inventors: Jerry K. Goff, Ambler; Joseph A. Marinko, Jr., Chalfont; Joseph G. Venditto, Jr., Perkasie; Donald A. Yost, Norristown, all of Pa.

[73] Assignee: Performance Controls Company, Hatboro, Pa.

[21] Appl. No.: 573,903

[22] Filed: Jan. 26, 1984

[51] Int. Cl.$^4$ .......................... H02P 6/02; H03K 5/22
[52] U.S. Cl. ..................................... 318/254; 318/293; 318/300; 363/97; 307/236; 328/118
[58] Field of Search ........... 318/138, 254, 439, 254 A, 318/280, 281, 283, 291, 293, 294, 300; 323/259, 260; 363/97, 98; 307/236, 355; 328/118

[56] References Cited

U.S. PATENT DOCUMENTS

| | | | |
|---|---|---|---|
| 3,050,671 | 8/1962 | Moller | 318/254 X |
| 3,281,630 | 10/1966 | Liang | 318/138 |
| 3,324,369 | 6/1967 | Markakis | 318/696 X |
| 3,373,378 | 3/1968 | Cottrell | 318/138 X |
| 3,383,574 | 5/1968 | Manteuffel | 318/254 X |
| 3,517,289 | 6/1970 | Brunner et al. | 318/254 X |
| 3,518,517 | 6/1970 | Rainer | 318/254 |
| 3,609,486 | 9/1971 | Feldhoff et al. | 318/138 |
| 3,679,954 | 7/1972 | Hedrick | 318/254 |
| 3,706,924 | 12/1972 | Adler | 318/254 X |
| 3,757,183 | 9/1973 | Nola | 318/254 |
| 3,764,869 | 10/1973 | Woodbury | 318/254 X |
| 3,783,359 | 1/1974 | Malkiel | 318/254 |
| 3,866,099 | 2/1975 | Bourbeau | 318/254 |
| 3,942,081 | 3/1976 | Liska et al. | 318/254 X |
| 3,946,292 | 3/1976 | Tanikoshi | 318/254 X |
| 4,008,425 | 2/1977 | Dickey | 318/254 X |
| 4,011,487 | 3/1977 | Loomis | 318/254 X |
| 4,025,835 | 5/1977 | Wada | 318/254 |
| 4,114,073 | 9/1978 | Uzuka | 318/254 X |
| 4,228,384 | 10/1980 | Arnold, Jr. et al. | 318/254 |
| 4,258,299 | 3/1981 | Takeda et al. | 318/254 X |
| 4,262,237 | 4/1981 | Gelenius | 318/254 |
| 4,270,074 | 5/1981 | Duckworth et al. | 318/138 X |
| 4,282,464 | 8/1981 | Uzuka | 318/254 X |
| 4,296,362 | 10/1981 | Beasley | 318/254 X |
| 4,338,551 | 7/1982 | Mizumoto | 318/254 |
| 4,354,145 | 10/1982 | Janssen | 318/254 |
| 4,409,524 | 10/1983 | Nielsen et al. | 318/138 |
| 4,454,454 | 6/1984 | Valentine | 318/339 X |
| 4,494,181 | 1/1985 | Ramlohr et al. | 318/293 X |

FOREIGN PATENT DOCUMENTS 0082392 6/1983 European Pat. Off. ............ 318/293

Primary Examiner—William M. Shoop, Jr.
Assistant Examiner—Bentsu Ro
Attorney, Agent, or Firm—Seidel, Gonda, Goldhammer

[57] ABSTRACT

An apparatus for use with an amplifier regulates the current through a load according to a drive signal having first and second states and comprises switchless sensing means and polarity correction means. The switchless sensing means provides a sense signal continuously representative of the magnitude of the current through the load without the use of switching circuitry. The polarity correction means is directly coupled to the sensing means and receives the sense signal and is responsive to the status of the drive signal for providing an analog signal continuously representative of both the instantaneous magnitude and polarity of the current through the load.

22 Claims, 9 Drawing Figures

TIMING DIAGRAMS

CURRENT SENSE DEMODULATOR

BACKGROUND OF THE INVENTION

The present invention relates generally to an apparatus and method for providing a feedback signal repesentative of the current through a load driven by a current amplifier. The present invention has particular application in constructing a feedback signal representative of the torque producing current through a multi-phase bushless DC motor driven by a pulse width modulated (PWM) amplifier, but is not limited thereto.

For explanation purposes only, the following discussion relates to the current sensing problem in multi-phase brushless DC motors and a solution for it. It will be understood, however, that the herein described invention is not limited in application to brushless DC motors.

Brushless DC motors are known. In such motors, a plurality of fixed stator windings and rotatable magnetic poles are provided. Motor rotation results by energizing each stator winding in a proper sequence. A proper sequence is one wherein a stator winding is energized when a torque producing magnetic pole is aligned with it. Generally, logic circuitry is provided which energizes the stator windings in the proper sequence. This logic circuitry requires as an input a drive signal which alternates between two states, such as a PWM signal. In order to determine the proper duty cycle of the PWM signal for a given load and a desired speed, the circuit generating the PWM signal requires a feedback signal containing information relating to both the instantaneous polarity and magnitude of the torque producing current through the stator windings.

Prior art current sensing schemes for providing feedback information to the PWM signal genration circuitry generally sense the current in each individual motor phase. The signals obtained from each motor phase are summed together to construct a waveform representative of the magnitude of the torque producing current. This is usually accomplished by placing a sense resistor in series with each motor phase, amplifying the voltage developed across each resistor and summing the amplified outputs together in the proper sequence. Summing the outputs together in the proper sequence is usually achieved by supplying the signal from each sense resistor to a separate solid state switch; the switch outputs are tied together in common and are opened and closed in the proper sequence under control of external logic. The external logic requires as an input the signal from an angular position sensor located within the motor. This sensor provides information relative to the angular position of the rotating magnetic poles.

The signal provided by the above described circuitry is representative of the instantaneous magnitude of the torque producing current, but because of the current induced by the motor's inductance, it is not necessarily representative of the correct polarity of the torque producing current.

To obtain a signal which is representative of both the instantaneous magnitude and polarity of the torque producing current, the prior art requires the use of additional circuitry. This additional circuitry is responsive to the PWM signal to pass the above described feedback signal in an inverted form when the PWM signal is in one state and in a non-inverted form when the PWM signal is in the other state.

It will be appreciated from the foregoing discussion that prior art current sensing schemes have two major drawbacks. First, in multi-phase loads, each phase requires a sense resistor and accompanying circuitry for providing a signal indicative of the magnitude of the instantaneous current through that phase. Second, circuitry is required for summing each of the phase signals in the proper sequence and for correcting the polarity of the signal obtained from the summation. In multi-phase brushless DC motors, this has required the use of an angular position sensor associated with the motor. Thus, prior art circuits for constructing a feedback signal representative of both the instantaneous magnitude and polarity of the torque producing motor current are cumbersome, expensive, and require complex logic.

It is therefore desirable to provide a circuit for generating a current signal continuously representative of both the instantaneous polarity and magnitude of the current through a load which is simple and requires few components. Such a signal can typically be used for feedback purposes but is not limited to such applications.

It is also desirable to provide a circuit for generating a current feedback signal continuously representative of both the instantaneous polarity and magnitude of the current through a multi-phase load which does not require a sense resistor for each phase and which does not require that multiple sense signals from the phases be summed together.

It is further desirable to provide a circuit for generating a current feedback signal continuously representative of both the instantaneous polarity and magnitude of the torque producing current in a multi-phase brushless DC motor which requires only a single sense resistor and does not require an angular position sensor associated with the motor to reproduce the signal and yet is simple, reliable, and inexpensive.

SUMMARY OF THE INVENTION

Apparatus for providing a current signal continuously representative of both the instantaneous magnitude and polarity of the current through a load driven by a current amplifier which regulates the current through the load according to the duty cycle of a drive signal having first and second states comprises sensing means for providing a sense signal representative of the magnitude of the current through the load and polarity correction means responsive to the drive signal for supplying the sense signal in an inverted form when the drive signal is in the first state and for supplying the sense signal in a non-inverted form when the drive signal is in the second state. The apparatus requires only a single sensing means (resistor) regardless of the number of phases in the load and hence does not require circuitry for summing individual phase signals together. As applied to brushless DC motors, the apparatus does not require an angular position sensor associated with the motor to produce a feedback signal which is representative of both the magnitude and polarity of the torque producing current. A feature of the present invention is that the polarity correction means is directly coupled to the sensing means, as opposed to the hereinbefore described prior art devices which require an intermediate switching network to sum the load currents from each phase.

In a preferred embodiment, the current amplifier is a full wave commutation bridge circuit receiving a source of electric current from a power supply and the drive signal is a pulse width modulation (PWM) signal. The load is connected across the bridge circuit. The sensing means comprises a single sense resistor connecting the bridge circuit to the return path of the power supply such that the current through the load flows through the sense resistor. The voltage developed across the sense resistor is a sense signal representative of the magnitude of the current through all phases of the load.

In one embodiment, the polarity correction means comprises switch means and differential input amplifier means wherein the switch means is responsive to the PWM signal to supply the sense signal to the inverting input of the differential input amplifier means when the PWM signal is in a first state and to supply the sense signal to the non-inverting input of the differential input amplifier when the PWM signal is in a second state. The output of the differential amplifier means thereby supplies the sense signal in an inverted form when the PWM signal is in the first state and in a non-inverted form when the PWM signal is in the second state. The output signal from the differential amplifier means is an analog current feedback signal.

In another embodiment, the polarity correction means comprises first and second switch means and first and second differential amplifier means and the sense signal is supplied to the inverting input of the first differential input amplifier means and to the non-inverting input of the second differential amplifier means. The first differential amplifier means is effective to supply the sense signal in an inverted form. The second differential input amplifier means is effective to supply the sense signal in a non-inverted form. The input of the first switch means is operatively connected to the output of the first differential input amplifier means and is responsive to pass the output of the first differential amplifier means only when the PWM signal is in the first state. The second switch means is operatively connected to the output of the second differential amplifier means and is responsive to pass the output of the second differential amplifier means only when the PWM signal is in the second state. The output of the first and second switch means are tied together in common. The output signal from the first and second switch means is the current feedback signal.

In still another embodiment, an intentional dead time is introduced into the PWM drive signal to prevent the bridge circuit from shorting during transition times of the PWM signal. Differential input amplifier means and switching means are responsive to first and second switching signals derived from the PWM signal for providing the sense signal in an inverted form when the first switching signal is in an active state and for providing the sense signal in a non-inverted form when the second switch signal is in an active state. A time delay is interposed between subsequent occurrences of the active states of the first and second switching signals and the time delay substantially corresponds to the dead time introduced into the PWM drive signal. Buffer means are provided at the output of the differential input amplifier and switching means to hold during the time delay period the last output provided by the differential input amplifier and switching means before the time delay occurred.

As applied to multiphase loads, an advantage of the present invention is that only a single resistor is required, regardless of the number of phases in the load and the circuitry for generating the current feedback signal is the same regardless of the number of phases in the load. As applied to multi-phase brushless DC motors, an additional advantage of the present invention is that an angular position sensor is not required to generate a feedback signal representative of both the polarity and magnitude of the load current. A further advantage is that the intermediate switching network for summing each of the phase load currents together required by prior art devices is eliminated. Still a further advantage is that the feedback signal is an analog signal which is continuously representative of both the instantaneous magnitude and polarity of the load current.

DETAILED DESCRIPTION OF THE DRAWINGS

Figure 1:
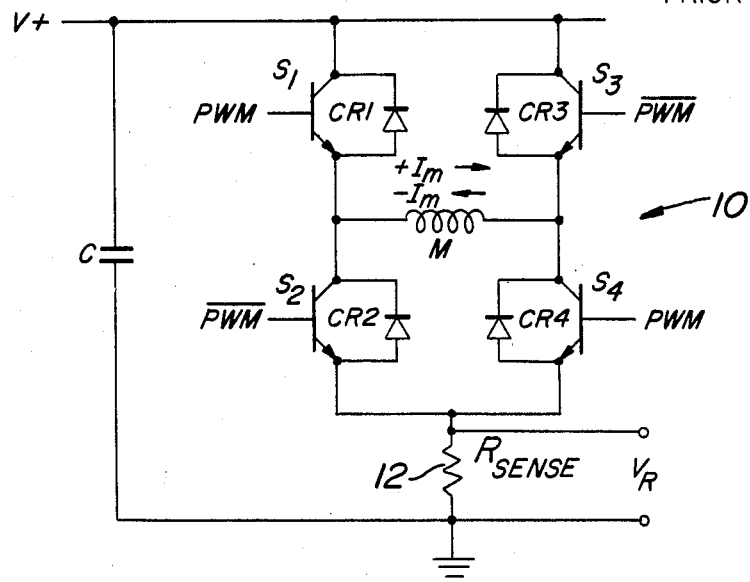
FIG. 1 illustrates a full wave commutation bridge driving a single phase load.

Referring now to the drawings wherein like numerals represent like elements, there is shown in FIG. 1 a current amplifier embodied as a full wave commutation bridge circuit 10 driving a motor load M. Full wave commutation bridge circuit comprises transistors S1, S2, S3 and S4 and associated diodes CR1, CR2, CR3, and CR4. Motor load M is connected across bridge circuit 10 as shown. One side of bridge circuit 10 is connected to a source of electrical power V+. A sense resistor 12 connects the other side of bridge circuit 10 to the return path of the power supply V+. A capacitor C is typically, but not necessarily, connected across the power supply terminals as shown.

Figure 2:
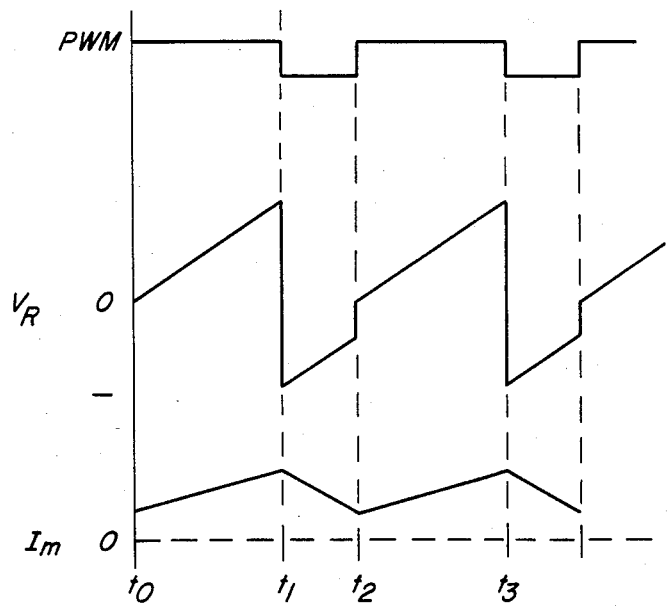
FIG. 2 illustrates the waveforms of the PWM drive signal, the sense signal and the actual motor load current.

The base of transistors S1 and S4 receive a PWM drive signal. The base of transistors S2 and S3 receive the inverted PWM drive signal, herein designated as $\overline{PWM}$. It will be appreciated that when the PWM signal is in a high state (logic 1), transistors S1 and S4 will become conductive and that transistors S2 and S3 will be non-conductive. Current flows from the power supply V+ through transistor S1, motor load M, transistor S4, sense resistor 12, and through the return path to the power supply. As shown in FIG. 2, during the time that the PWM signal is in the high or logic 1 state (i.e., between time $t_0$ and $t_1$) the motor current $I_M$ is increasing at a finite rate due to the inductance of motor load M. During this time the voltage $V_R$ across sense resistor 12 is positive and increasing as shown in FIG. 2. When the PWM signal changes to the low (logic 0) state at time $t_1$, transistors S1 and S4 become non-conductive.

The $\overline{\text{PWM}}$ signal becomes high (logic 1) and transistors S2 and S3 saturate and become conductive. However, the inductance of motor M prevents the current $I_M$ from reversing instantly. Instead, the motor current decays in magnitude via the path defined by diode CR3, capacitor C, sense resistor 12 and diode CR2. This is shown in FIG. 2 between times $t_1$ and $t_2$. During this time, the voltage $V_R$ across sense resistor 12 is of negative polarity and decreasing magnitude as shown in FIG. 2. At time $t_2$, PWM again becomes high (logic 1), transistors S2 and S3 become nonconductive and transistors S1 and S4 become conductive. The motor current $I_M$ becomes positive and increases as shown in FIG. 2 between times $t_2$ and $t_3$. It will be appreciated that the speed and torque of motor M, are regulated according to the duty cycle of the PWM drive signal.

The actual motor current $I_M$ is shown in FIG. 2. It can be seen that, given only the PWM signal and the sense signal $V_R$, an accurate representation of both the magnitude and polarity of the motor current $I_M$ can be reconstructed without using an angular position sensor. This is achieved by passing the sense signal $V_R$ unchanged when the PWM signal is high (logic 1) and inverting the sense signal $V_R$ when the PWM signal is low (logic 0).

Figure 3:
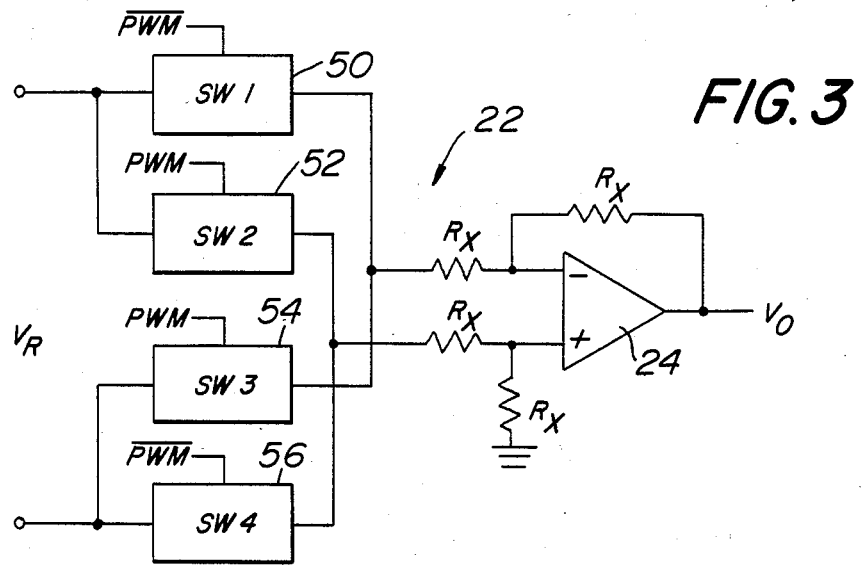
FIG. 3 illustrates a current feedback circuit according to one embodiment of the invention.

FIG. 3 illustrates one embodiment of a circuit which utilizes the PWM signal and the sense signal $V_R$ to construct a waveform representative of both the polarity and magnitude of the torque producing motor current $I_M$.

Referring to FIG. 3, circuit 22 comprises switch means 50, 52, 54 and 56 and differential input amplifier means 24. As shown, switches 50 and 56 are responsive to the $\overline{\text{PWM}}$ signal and switches 52 and 54 are responsive to the PWM signal. Thus, when the $\overline{\text{PWM}}$ signal is active (logic 1), switches 50 and 56 will be closed and switches 52 and 54 will be open. Alternatively, when the PWM signal is active (logic 1), switches 52 and 54 will be closed and switches 50 and 56 will be open.

When the $\overline{\text{PWM}}$ signal is active (logic 1), differential input amplifier 24 is configured as an inverting amplifier and therefore the sense signal $V_R$ is applied to the inverting input of differential amplifier 24. The signal $V_O$ at the output $V_O$ of differential input amplifier 24 is an inverted form of the sense signal $V_R$.

When the PWM signal is active (logic 1), differential amplifier 24 is configured as a non-inverting amplifier. The sense signal $V_R$ is applied to the non-inverting input of differential input amplifier 24. The signal $V_O$ at the output of differential input amplifier 24 is a non-inverted form of the sense signal $V_R$.

Referring back to FIG. 2, it will be appreciated that the output signal $V_O$ of differential input amplifier 24 corresponds to the motor current waveform $I_M$. It will be seen therefore, that the circuit of FIG. 3 provides an analog current signal which is continuously representative of both the instantaneous magnitude and polarity of the torque producing motor current $I_M$.

Figure 4:
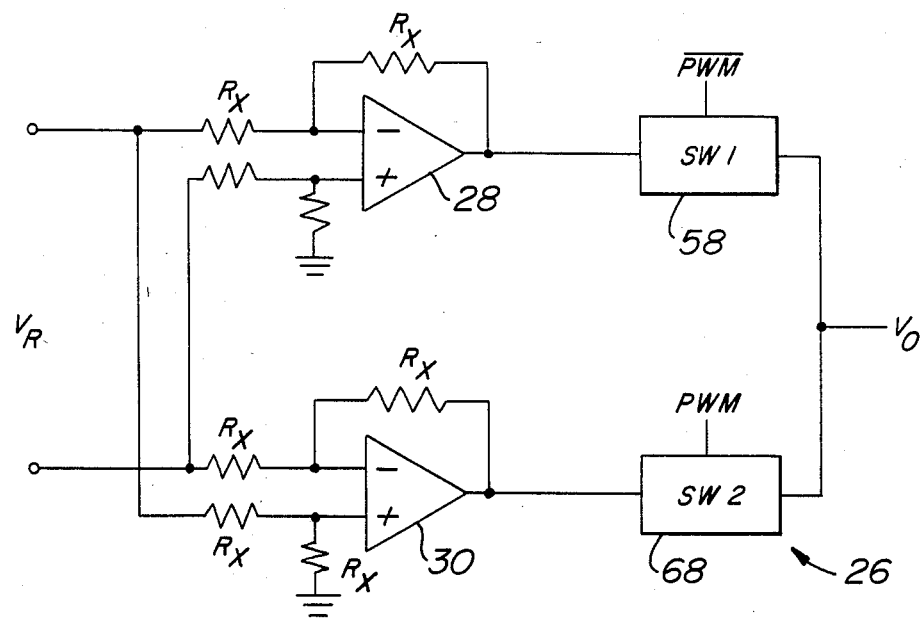
FIG. 4 illustrates a current feedback circuit according to another embodiment of the invention.

Referring now to FIG. 4, there is shown a second embodiment of a circuit which utilizes the PWM drive signal and the sense signal $V_R$ to provide a current signal representative of both the instantaneous magnitude and polarity of the torque producing motor current $I_M$.

Circuit 26 comprises first and second differential input amplifier means 28 and 30 and first and second switch means 58 and 68. As shown, differential input amplifier 28 receives the sense signal $V_R$ on its inverting input (and therefore inverts the sense signal $V_R$) and differential input amplifier 30 receives the sense signal $V_R$ on its non-inverting input (and therefore passes the sense signal $V_R$ non-inverted). The output of amplifier 28 is supplied to the input of a switch 58. The output of differential input amplifier 30 is supplied to the input of a switch 68. The outputs of switches 58 and 68 are tied together in common as shown. Switch 58 closes when the $\overline{\text{PWM}}$ signal is active (logic 1) and switch 68 closes when the PWM signal is active (logic 1).

An inverted form of the sense signal $V_R$ is passed through switch 58 and supplied as the output signal $V_O$ when the $\overline{\text{PWM}}$ signal is active (logic 1). A non-inverted form of the sense signal $V_R$ is passed through switch 68 and supplied as the output signal $V_O$ when the PWM signal is active (logic 1).

It will be appreciated that the output signal $V_O$ substantially corresponds to the motor current $I_M$ shown in FIG. 2. The output $V_O$ is therefore an analog current signal which is continuously representative of both the instantaneous polarity and magnitude of the torque producing motor current $I_M$.

Figure 5:
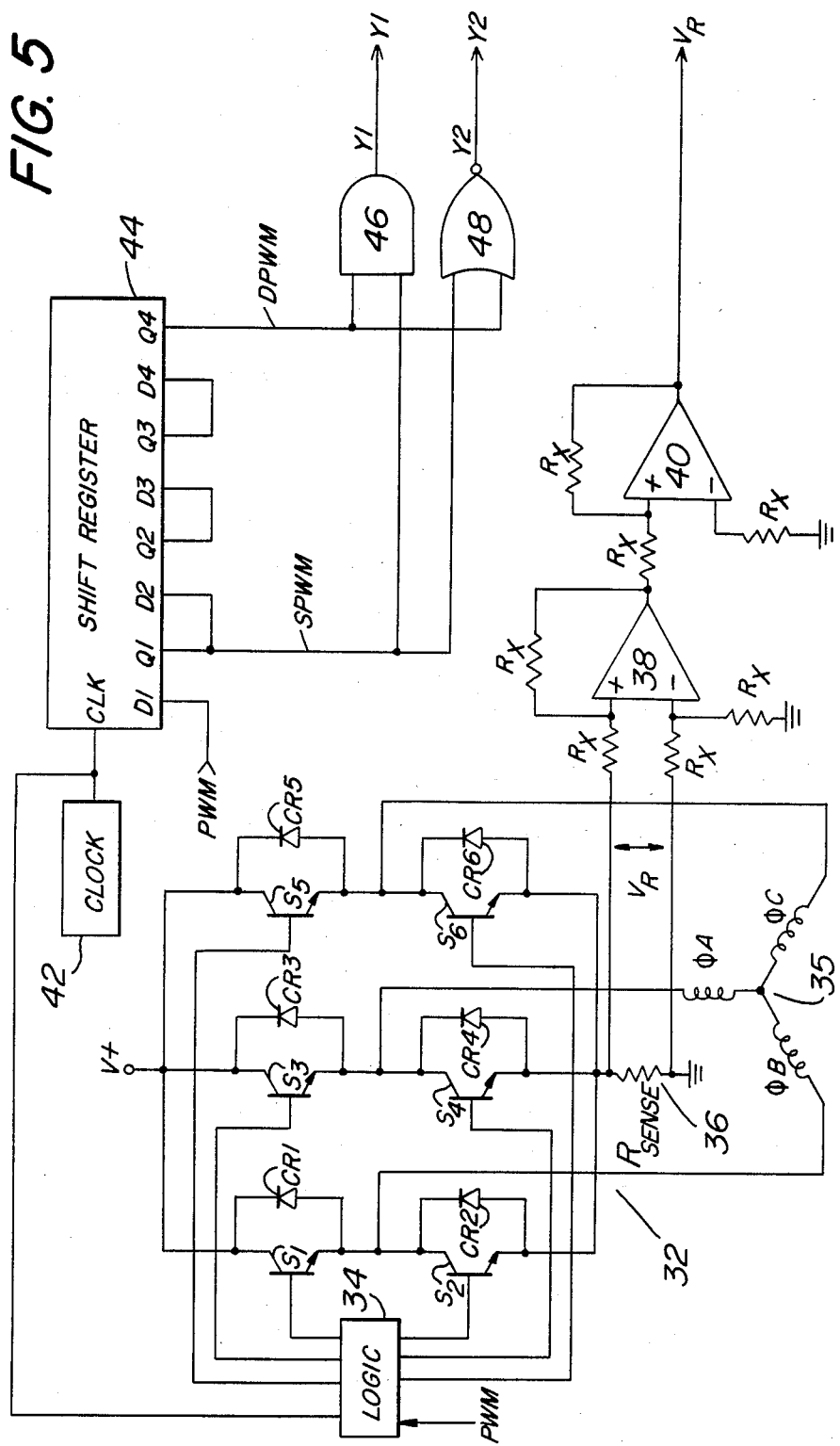
FIG. 5 illustrates a full wave bridge circuit driving a three phase load and the circuitry for deriving the first and second switching signals from the PWM drive signal.

Referring now to FIG. 5, a full wave commutation bridge 32 driving a three phase brushless DC motor is shown. Full wave commutation bridge 32 comprises transistors S1–S6 and associated diodes CR1–CR6. One side of the bridge circuit 32 is connected to a power supply V+. The other side of the bridge circuit is connected via a sense resistor 36 to the return path of the power supply.

A PWM signal is applied to a logic circuit 34. Logic circuit 34 also receives clock pulses from a clock 42. Logic circuit 34 applies the PWM signal to the transistors S1–S6 in the proper sequence to insure rotation of brushless DC motor 35 in well-known manner. A typical energization sequence for transistors S1–S6 is shown in the following table.

| Displacement | Current Flow | "On" Transistors |
| --- | --- | --- |
| 0–60° | ØA to ØB | S3, S2 |
| 60°–120° | ØA to ØC | S3, S6 |
| 120°–180° | ØB to ØC | S1, S6 |
| 180°–240° | ØB to ØA | S1, S4 |
| 240°–300° | ØC to ØA | S5, S4 |
| 300°–360° | ØC to ØB | S5, S2 |

It will be appreciated that the motor current $I_M$ through any of the phases ɸA, ɸB, and ɸC of brushless DC motor 35 will also flow through sense resistor 36. For example, when transistors S1 and S4 are turned on, current flows from power supply V+, through transistor S1, through phases ɸB and ɸA, through transistor S4 and sense resistor 36. The voltage $V_R$ developed across sense resistor 36 is representative of the instantaneous motor current $I_M$ through all phases of the motor M.

The sense signal $V_R$ is applied to a double buffer amplifier circuit comprising differential input amplifiers 38 and 40. The buffer amplifiers remove any ground differential error and provide sufficient gain to sense signal $V_R$ to preserve the signal to noise ratio prior to subsequent processing. Thus, as used in connection with this embodiment, the sensing means includes not only the resistor 36, but the amplifiers 38, 40, and the sensing means is still directly coupled to the polarity correction means, as will become evident hereinafter.

The previous discussion has been based on the premise that the transistors comprising the bridge circuit will instantaneously turn off when the PWM or $\overline{\text{PWM}}$ drive signal changes to its inactive state (i.e. changes from logic 1 to logic 0). However, in practical circuits utilizing transistor type bridge circuits, instantaeous turn-off of the transistors is not realizable. For example, referring to FIG. 1, when the PWM signal changes from logic 1 to logic 0, transistor S1 does not turn fully off before transistor S2 turns on. This is because a finite amount of time is required for transistor S1 to come out of saturation after the PWM drive signal changes to its inactive state (logic 0). This results in simultaneous conduction of transistors S1 and S2. Since transistors S1 and S2 form a series connection across the power supply V+, their simultaneous conduction results in excessive current and the destruction of transistors of S1 and S2.

Figure 8A:
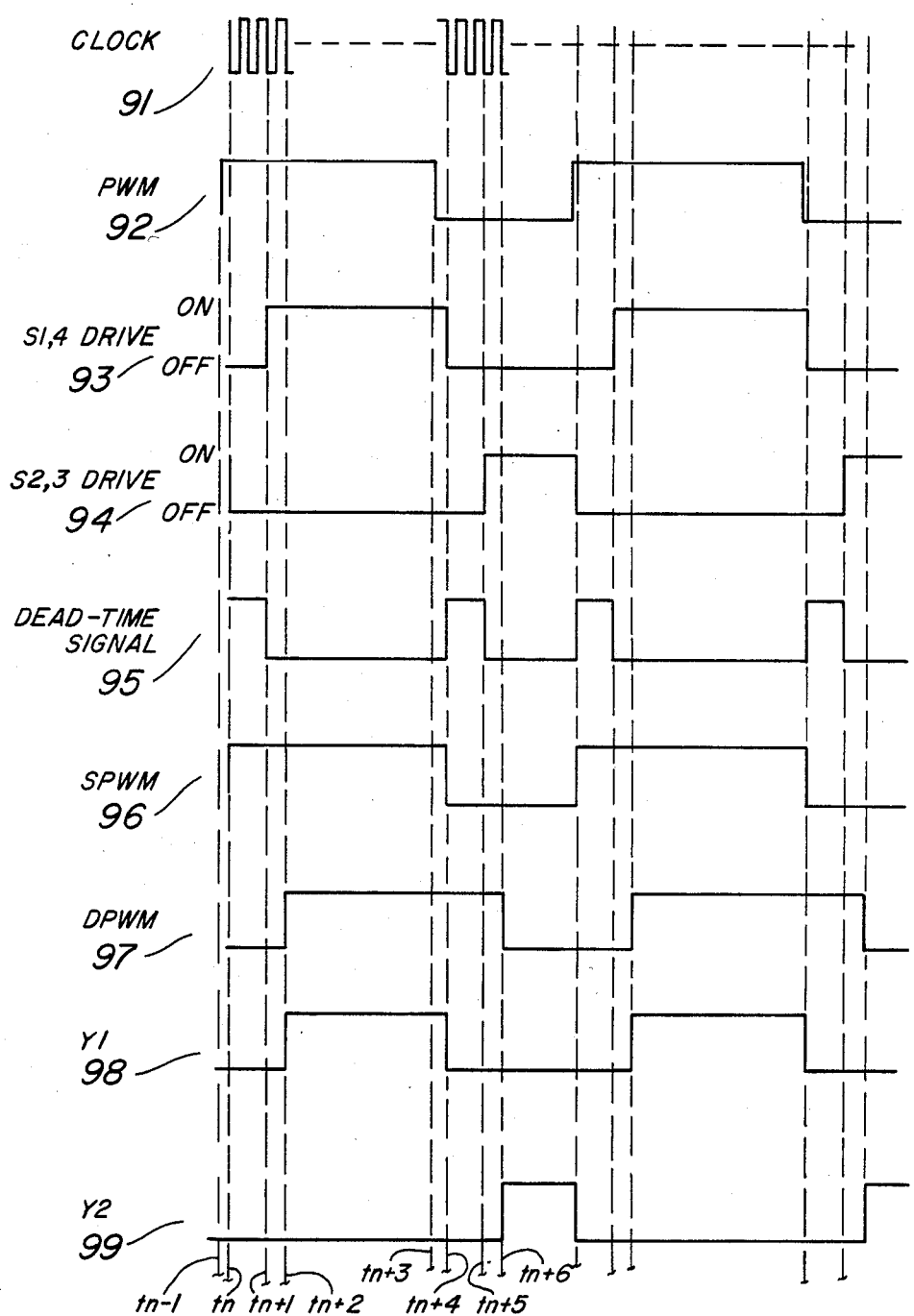
FIGS. 8A and 8B illustrate various timing diagrams associated with the practice of the present invention.

To avoid this problem, an intentional "dead time" is introduced into the PWM and $\overline{\text{PWM}}$ signals driving the bridge circuit, via logic circuit 34. Referring to FIG. 8A, it will be explained how a dead time is introduced into the PWM and $\overline{\text{PWM}}$ signals which are applied to transistors S1–S4 in the bridge circuit 10 in FIG. 1.

A dead time signal 95 is generated by logic circuit 34. As shown, the dead time signal 95 is a train of pulses wherein each pulse is approximately two clock periods in duration. Circuitry in logic circuit 34 is responsive to dead time signal 95 to provide a time delay between the occurrence of the active state of drive signal 93 for transistors S1 and S4 and the active state of drive signal 94 for transistors S2 and S3. The duration of the time delay is sufficient to insure that all transistors are "off" before allowing a transistor pair in the bridge circuit to turn "on". It will be noted that the duration of the time delay is substantially equal to the duration of the pulse in the dead time signal 95.

Due to the time delay introduced into transistor drive signals 93 and 94, the PWM and $\overline{\text{PWM}}$ signals can no longer be used to directly control the circuitry of FIGS. 3 and 4. Additional circuitry which will compensate for the time delay introduced into the transistor drive signals is required.

Embodiments of the invention which incorporate the inventive principles described above and which contain circuitry to compensate for the time delay are now described.

Referring again to FIG. 5, there is shown a four stage serial shift register 44. Shift register 44 receives a source of clock pulses from clock 42 via its clock input CLK. The PWM signal is applied to the input of the first stage D1 of shift register 44. The output of the last stage Q4 of shift register 44 is applied to one input of an AND gate 46 and to one input of a NOR gate 48. The output of an intermediate stage, herein shown as the output of the first stage, Q1, is applied to the other input of AND gate 46 and to the other input of NOR gate 48. For reference purposes, the output of the intermediate stage Q1 is labelled SPWM and the output of the last stage Q4 is labelled DPWM.

For purposes of the following explanation, it will be assumed that the CLK input of shift register 44 is responsive to the negative edge of the clock pulses supplied by clock 42. Thus, data in shift register 44 is clocked by one stage upon the occurrence of a negative going clock pulse edge. As shown in FIG. 8A, the occurrence of the SPWM signal 96 substantially coincides with the occurrence the PWM signal 92 except as herein noted. As shown, the PWM signal 92 goes high at time $t_n - 1$. At time $t_n$, the negative-going edge of a clock pulse 91 coincides with the high state of the PWM signal 92 and clocks a "1" into the first stage of the shift register 44 thereby causing the SPWM signal 96 to become high. The PWM signal 92 remains high until time $t_n + 3$ at which time it becomes low. A short time thereafter, at time $t_n + 4$, which coincides with the first occurrence of a negative-going clock pulse edge after the PWM signal goes low, a "0" is clocked into the first stage of the shift register 44 and the SPWM signal 96 goes low. This process repeats itself, as shown in FIG. 8A.

As will be understood, the signal DPWM, which is the output of the last stage Q4 of shift register 44, will be delayed by three clock periods relative to the SPWM signal 96. This is illustrated in FIG. 8A. As shown, the occurrence of the DPWM signal 97 coincides with the occurrence of the negative-going edge of the third clock pulse after the SPWM signal 96 occurred. Thus, the DPWM signal 97 becomes high at time $t_n + 2$ and goes low three clock periods after the SPWM signal goes low at time $t_n + 6$.

The logic circuit comprising AND gate 46 and NOR gate 48 combines the SPWM and DPWM signals to supply first and second switching signals Y1 and Y2. As shown in FIG. 8A, the Y1 switching signal 98 substantially coincides with the S1, S4 drive signal 93 except that its occurrence is delayed by one clock period. Similarly, the Y2 switching signal 99 substantially coincides with the S2, S3 drive signal 94 except that its occurrence is also delayed by one clock period. Switching signals Y1 and Y2 are active high, i.e., each is active when it is a logic 1.

It will be appreciated from an examination of FIG. 8A that there is a time delay between the occurrence of the active state of the Y1 switching signal 98 and the occurrence of the active state of the Y2 switching signal 99. This time delay substantially corresponds to the duration of the pulses in the dead time signal 95 except that it exceeds the duration of the pulses in dead time signal by one clock period. Switching signals Y1 and Y2 may be applied to circuitry similar to that shown in FIGS. 3 and 4 for converting the sense signal $V_R$ into an analog current feedback signal which is continuously representative of both the magnitude and polarity of the torque producing motor current $I_M$.

Figure 6:
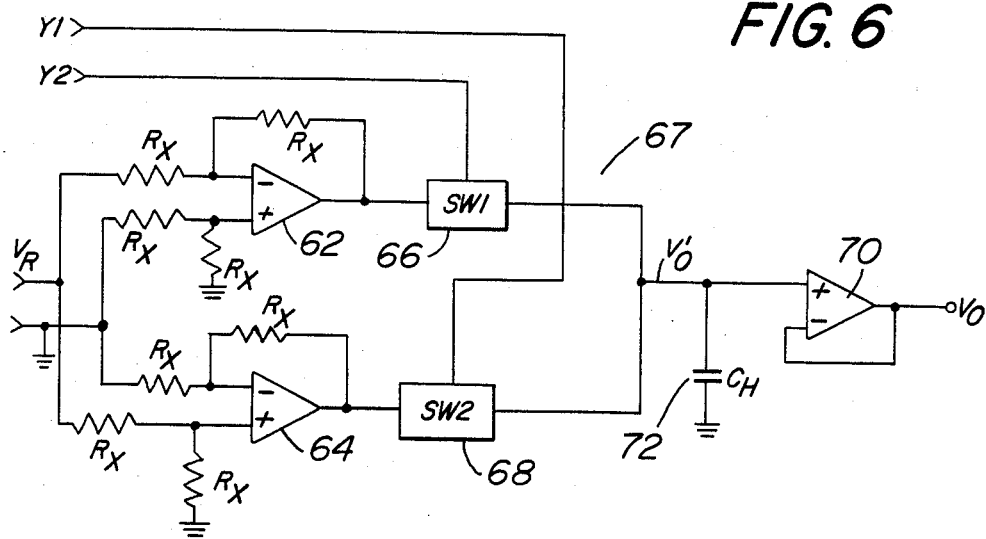
FIG. 6 illustrates a circuit for providing a current feedback signal according to another embodiment of the invention.

Turning now to FIG. 6, there is shown a circuit which is responsive to the switching signals Y1 and Y2 and to the sense signal $V_R$ for providing an analog current feedback signal $V_O$.

Circuit 67 comprises first and second differential input amplifiers 62 and 64 and first and second switches 66 and 68. Differential input amplifier 62 receives the sense signal $V_R$ on its inverting input and is effective to pass the sense signal $V_R$ is an inverted form. Differential input amplifier 64 receives the sense signal $V_R$ on its non-inverting input and is effective to pass the sense signal $V_R$ in a non-inverted form. The output of amplifier 62 is connected to the input of switch 66. Switch 66 is responsive to switch signal Y2 such that switch 66 closes when switch signal Y2 is active (logic 1) and opens when it is inactive (logic 0). The output of amplifier 64 is provided to the input of switch 68. Switch 68 is responsive to switch signal Y1 such that switch 68 closes when switch signal Y1 is active (logic 1) and opens when it is inactive (logic 0). The outputs of switches 66 and 68 are tied together in common as shown.

Figure 8B:
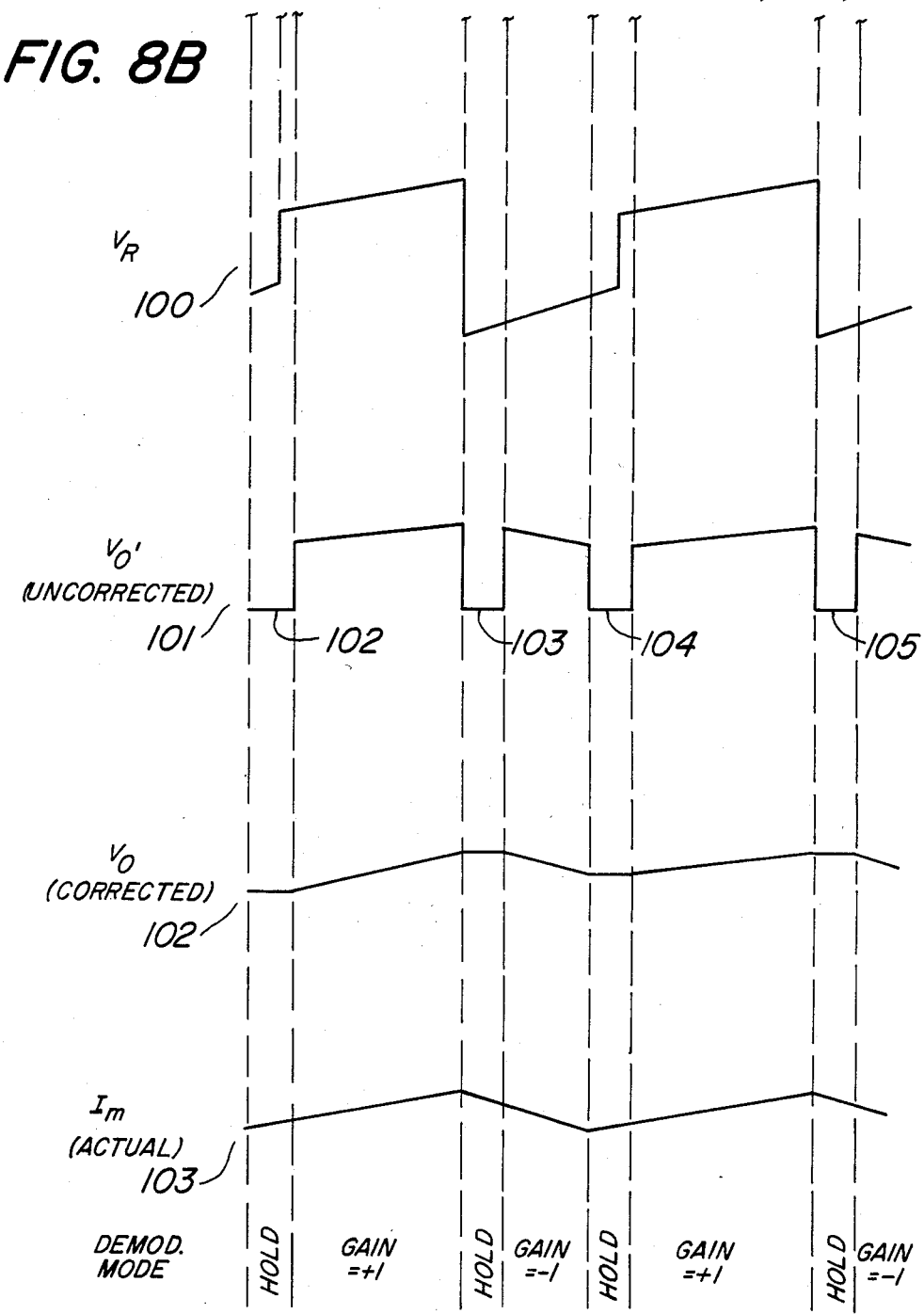

When switch signal Y1 is active, the sense signal $V_R$ is passed in a non-inverted form through switch 68. When switch signal Y2 is active, the sense signal $V_R$ is passed in an inverted form through switch 66. Assuming that circuitry comprising amplifier 70 and holding capacitor 72 were not provided, the signal $V_O'$ 101 shown in FIG. 8B would result. The "gaps" 102, 103, 104 and 105 which occur in the $V_O'$ signal 101 are directly attributable to the time delay interposed between subsequent occurrences of the active states of switching signals Y1 and Y2 and are indirectly attributable to the time delay introduced into the transistor drive signals. Circuitry comprising amplifier 70 and holding capacitor 72 is provided to correct the $V_O'$ signal. Holding capacitor 72 holds during the time delay the last value supplied by switches 66 and 68 before the time delay occurred. At all other times, holding capacitor 72 and therefore amplifier 70 follow the signal $V_O'$. The addition of amplifier 70 and holding capacitor 72 results in a corrected signal $V_O$ 102 which is shown in FIG. 8B. As can be seen, the output signal $V_O$ substantially corresponds to the actual current waveform $I_M$ 103.

Figure 7:
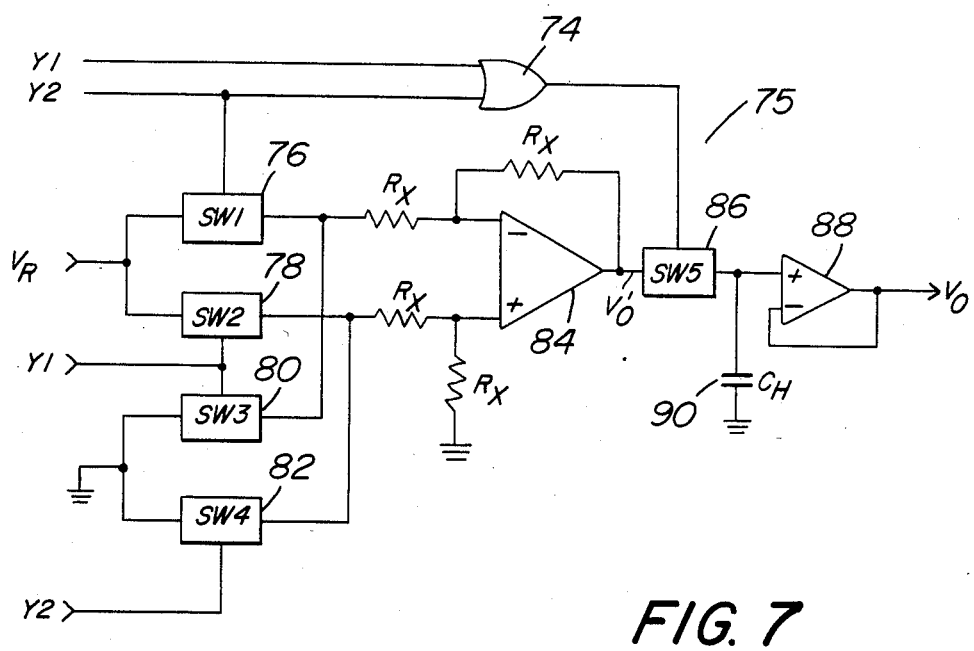
FIG. 7 illustrates a circuit for generating a current feedback signal according to still another embodiment of the invention.

Another circuit which uses the Y1 and Y2 switching signals and the sense signal $V_R$ and generates a current signal is shown in FIG. 7.

Circuit 75 comprises differential input amplifier 84 and first switch means 76, 82 and second switch means 78, 80. A third switch means 86 is also provided for purposes which will become evident hereinafter.

Switches 76 and 82 are responsive to the second switch signal Y2 and close when switch signal Y2 is active (logic 1) and open when it is in inactive (logic 0). Switches 78 and 80 are responsive to the switch signal Y1 and close when switch signal Y1 is active (logic 1) and open when it is inactive (logic 0). It will be seen that when switch signal Y2 is active, the sense signal $V_R$ will be applied to the inverting input of amplifier 84. Amplifier 84 will thereby be effective to pass the sense signal $V_R$ in an inverted form to the input of switch 86. Alternatively, when switch signal Y1 is active, the sense signal $V_R$ is applied to the non-inverting input of amplifier 84. Amplifier 84 is thereby effective to pass the sense signal $V_R$ in a non-inverted form to the input of switch 86. It will be appreciated that the signal $V_O'$ appearing at the input of switch 86 corresponds to the signal $V_O'$ 101 as shown in FIG. 8B. Again, the "gaps" 102, 103, 104 and 105 are directly attributable to the time delay interposed between subsequent occurrences of the Y1 and Y2 switching signals and are indirectly attributable to the time delay introduced into the transistor drive signals. Circuitry comprising switch 86, amplifier 88 and holding capacitor 90 are provided to correct the signal $V_O'$ 101 and to obtain a corrected $V_O$ signal 102.

Switching signals Y1 and Y2 are supplied to the inputs of an OR gate 74. The output of OR gate 74 drives switch 86. It will be appreciated that switch 86 closes when either switching signal Y1 or Y2 is active (logic 1) and is open when both of the switching signals are inactive (logic 0). Stated otherwise, the switch 86 is open during the time delay period. The holding capacitor 90 holds during the time that switch 86 is open the last value supplied by amplifier 84 before switch 86 opened; that is, holding capacitor 90 holds during the time delay the last value supplied by amplifier 84 before the time delay occurred. When switch 86 is closed, the output of amplifier 88 follows the signal provided by amplifier 84. It will be appreciated that the signal $V_O$ provided by the amplifier 88 corresponds to the signal $V_O$ 102 shown in FIG. 8B. As seen, signal $V_O$ 102 accurately represents the motor current $I_M$ 103. Thus, signal $V_O$ 102 is an analog current feedback signal continuously representative of both the instantaneous polarity and magnitude of the torque producing motor current.

The functions performed by the circuits of FIGS. 6 and 7 are summarized at the bottom of FIG. 8B. As shown, when the Y1 switching signal 98 is active, the sense signal $V_R$ is passed in a non-inverted form, i.e., the gain of the circuit is $+1$. When the Y2 switching signal 99 is active, the sense signal $V_R$ is passed in an inverted form, i.e., the gain of the circuit is $-1$. During the time delay period, the circuitry holds the last value provided before the time delay occurred.

The present invention may be employed in other specific forms without departing from the spirit or essential attributes thereof and, accordingly, reference should be made to the appended claims, rather than to the foregoing specification, as indicating the scope of the invention.

We claim:

1. Apparatus for use with an amplifier regulating the current through a load according to a drive signal having first and second states comprising:
    (a) a single switchless sensing means disposed in a current path through which load current flows regardless of the polarity of the load current for providing a sense signal continuously representative of the magnitude of the current through the load without the use of switching circuitry;
    (b) polarity correction means directly coupled to the sensing means, receiving the sense signal and responsive to the status of the drive signal for providing an analog signal continuously representative of both the instantaneous magnitude and polarity of the current through the load.

2. Apparatus according to claim 1 wherein the polarity correction means further comprises means for supplying the sense signal in an inverted form when the drive signal is in the first state, for supplying the sense signal in a non-inverted form when the drive signal is in the second state and for providing a composite of the inverted and non-inverted forms of the sense signal, the composite being the analog signal.

3. Apparatus according to claim 1 wherein the amplifier is a full wave commutation bridge circuit having output terminals and first and second power input terminals, the first power input terminal being connected to one side of a power supply, the load being connected across the output terminals of the bridge circuit, the sensing means comprising a sense resistor connecting the second power input terminal to the return path of the power supply so that the current through the load flows through the sense resistor, the voltate across the sense resistor being the sense signal.

4. Apparatus according to claim 3 wherein the drive signal is a pulse width modulation (PWM) signal applied to drive signal input terminals of the full wave commutation bridge circuit for regulating the current through the load in accordance with the duty cycle of the PWM signal, the polarity correction means comprising switch means and differential input amplifier means, the switch means receiving the sense signal and being responsive to the PWM signal to supply the sense signal to the inverting input of the differential input amplifier means when the PWM signal is in the first state and to supply the sense signal to the non-inverting input of the differential input amplifier means when the PWM signal is in the second state, the output of the differential input amplifier means thereby supplying the sense signal in an inverted form when the PWM signal is in the first state and in a non-inverted form when the PWM signal is in the second state, the output of the differential input amplifier means being the analog signal.

5. Apparatus according to claim 3 wherein the drive signal is a pulse width modulation (PWM) signal applied to drive signal input terminals of the full wave commutation bridge circuit for regulating the current through the load in accordance with the duty cycle of the PWM signal, the polarity correction means comprising first and second switch means and first and second differential input amplifier means, the sense signal being supplied to the inverting input of the first differential input amplifier means and to the non-inverting input of the second differential input amplifier means, the first differential input amplifier means being effective to supply the sense signal in an inverted form at the output thereof, the second differential input amplifier means being effective to supply the sense signal in a non-inverted form at the output thereof, the first switch means being operatively connected to the output of the first differential input amplifier means and being responsive to pass the output thereof when the PWM signal is in the first state and not to pass the output thereof when the PWM signal is in the second state, the second switch means being operatively connected to the output of the second differential input amplifier means and being responsive to pass the output thereof when the PWM signal is in the second state and not to pass the output thereof when the PWM signal is in the first state, the first and second switch means thereby providing the analog signal.

6. Apparatus according to claim 4 or 5 wherein the load is a brushless DC motor.

7. Apparatus comprising:
(a) an amplifier driven by a pulse width modulation (PWM) signal for regulating the current supplied to a load;
(b) a single switchless sensing means disposed in a current path through which load current flows regardless of the polarity of the load current for providing a sense signal continuously representative of the magnitude of the current through the load without the use of switching circuitry;
(c) switching signal means for providing first and second switching signals derived from the PWM signal;
(d) polarity correction means directly coupled to the sensing means and receiving the sense signal and responsive to the first switching signal for supplying the sense signal in an inverted form during at least a portion of the time that the PWM signal is in a first state and to the second switching signal for supplying the sense signal in a non-inverted form during at least a portion of the time that the PWM signal is in a second state, the polarity correction means providing an analog signal continuously representative of both the instantaneous polarity and magnitude of the current through the load.

8. Apparatus according to claim 7 wherein the first switching signal is in an active state during at least a portion of the time the PWM signal is in the first state and is in an inactive state at all other times and the second switching signal is in an active state during at least a portion of the time the PWM signal is in the second state and in an inactive state at all other times and the switching signal means further comprises time delay means for interposing a time delay between the occurrence of the active states of the first and second switching signals.

9. Apparatus according to claim 8 wherein the amplifier is a full wave commutation bridge circuit having output terminals and first and second power input terminals for connection to a power supply, the first power input terminal being connected to the positive side of the power supply, the load being connected across the output terminals of the bridge circuit, the sensing means comprising a sense resistor connecting the second power input terminal of the bridge circuit to the return path of the power supply so that the current through the load flows through the sense resistor, the voltage across the sense resistor being the sense signal.

10. Apparatus according to claim 9 wherein the switching signal means comprises a plural stage shift register operatively connected to a logic circuit, the shift register having a clock input driven by a source of clock pulses, the PWM signal being supplied to the input of the first stage of the shift register, the logic circuit receiving the outputs of the last stage and a selected intermediate stage of the shift register and supplying the switching signals, the time delay between the occurrence of the first and second switching signals substantially corresponding to the clock period multiplied by the number of shift register stages between the last stage and the selected intermediate stage.

11. Apparatus according to claim 10 wherein the polarity correction means comprises first and second differential input amplifiers and first and second switch means, the sense signal being applied to the inverting input of the first differential input amplifier and to the non-inverting input of the second differential input amplifier, the output of the first differential input amplifier being applied to the first switch means and the output of the second differential input amplifier being applied to the second switch means, the first switch means being responsive to the first switching signal to pass the output of the first differential input amplifier only when the first switching signal is in the active state, the second switch means being responsive to the second switching signal to pass the output of the second differential amplifier only when the second switching signal is in the active state.

12. Apparatus according to claim 10 wherein the polarity correction means comprises a differential input amplifier and first and second switch means, the first and second switch means receiving the sense signal, the first switch means being responsive to the first switching signal to apply the sense signal to the inverting input of the differential input amplifier when the first switching signal is in the active state, the differential input amplifier thereby supplying the sense signal in an inverted form when the first switching signal is in the active state, the second switch means being responsive to the second switching signal to apply the sense signal to the non-inverting input of the differential input amplifier when the second switching signal is in the active state, the differential input amplifier thereby supplying the sense signal in a non-inverted form when the second switching signal is in the active state.

13. Apparatus according to claim 11 wherein the polarity correction means further comprises buffer amplifier means for receiving the signal from the first and second switch means and holding during the time delay the last value of the signal supplied by the first and second switch means before the time delay occurred.

14. Apparatus according to claim 12 wherein the polarity correction means means further comprises third switch means operatively connected to the output of the differential input amplifier for passing the output signal of the differential input amplifier only when either of the first or second switching signals is in the active state.

15. Apparatus according to claim 14 wherein the polarity correction means further comprises buffer amplifier means for receiving the signal from the third switch means and holding during the time delay the last value of the signal supplied by the third switch means before the time delay occurred.

16. Apparatus according to claim 13 or 15 wherein the load is a brushless DC motor.

17. Apparatus for providing a current feedback signal continuously representative of instantaneous polarity and magnitude of the load current through a brushless DC motor regulated by a full wave commutation bridge which is driven by a pulse width modulation (PWM) signal and which receives a source of current from a power supply, comprising:
 (a) a sense resistor connecting the bridge circuit to the return path of the power supply so that the current through the load flows through the sense resistor, the voltage across the sense resistor defining a sense signal;
 (b) a plural stage shift register which is clocked by a source of clock pulses, the input of the first stage of the shift register receiving the PWM signal, the outputs of the last stage and a selected intermediate stage of the shift register being supplied to a logic circuit, the logic circuit providing first and second switching signals, the switching signals each having an active state and an inactive state, the first switching signal being active during at least a portion of the time that the PWM signal is in a first state and being inactive at all other times, the second switching signal being active during at least a portion of the time that the PWM signal is in a second state and being inactive at all other times, the shift register providing a time delay between subsequent occurrences of the active state of the first and second switching signals, the duration of the time delay substantially corresponding to the clock period multiplied by the number of stages between the last stage and the selected intermediate state of the shift register;
 (c) differential input amplifier and switch means responsive to the first and second switching signals for providing the sense signal in an inverted form when the first signal is in the active state and for providing the sense signal in a non-inverted form when the second signal is in the active state;
 (d) signal holding means receiving the signal provided by the differential input amplifier and switch means for holding during the time delay the last value of the signal supplied by the differential input and switch means before the time delay occurred.

18. A method of providing an analog signal continuously representative of both the instantaneous polarity and magnitude of the current through a load driven by a pulse width modulation (PWM) signal, the method comprising:
 (a) sensing the current through the load by means of a signle sensing element disposed in a current path through which load current flows regardless of the polarity of the load current and switchlessly providing a sense signal representative of the magnitude of the current through the load;
 (b) inverting the polarity of the sense signal during at least a portion of the time that the PWM signal is in a first state;
 (c) passing the sense signal in a non-inverted form during at least a portion of the time that the PWM signal is in a second state;
 (d) combining the signals obtained in steps (b) and (c) to obtain the analog signal.

19. Apparatus according to claim 1 wherein the load is a multi-phase load.

20. Apparatus according to claim 1 wherein the load current is a direct current.

21. Apparatus according to claim 7 wherein the load is a multi-phase load.

22. Apparatus according to claim 7 wherein the load current is a direct current.

* * * * *